United States Patent
Garinaud

(10) Patent No.: US 10,987,053 B2
(45) Date of Patent: Apr. 27, 2021

(54) METHOD AND SYSTEM FOR MEASURING AND DISPLAYING DATA LINKED TO A PERSON'S PHYSICAL ACTIVITY

(71) Applicant: Guenat SA Montres Valgine, Les Breuleux (CH)

(72) Inventor: Frédéric Garinaud, Le Noirmont (CH)

(73) Assignee: Guenat SA Montres Valgine, Les Breuleux (CH)

( * ) Notice: Subject to any disclaimer, the term of this patent is extended or adjusted under 35 U.S.C. 154(b) by 44 days.

(21) Appl. No.: 16/315,466

(22) PCT Filed: Jul. 6, 2017

(86) PCT No.: PCT/IB2017/054084
§ 371 (c)(1),
(2) Date: Jan. 4, 2019

(87) PCT Pub. No.: WO2018/007978
PCT Pub. Date: Jan. 11, 2018

(65) Prior Publication Data
US 2019/0307397 A1    Oct. 10, 2019

(30) Foreign Application Priority Data

Jul. 7, 2016 (CH) .................................... 00872/16
Feb. 24, 2017 (CH) .................................... 00216/17

(51) Int. Cl.
*A61B 5/00* (2006.01)
*G16H 20/30* (2018.01)
(Continued)

(52) U.S. Cl.
CPC ............ *A61B 5/681* (2013.01); *A61B 5/0015* (2013.01); *A61B 5/0017* (2013.01);
(Continued)

(58) Field of Classification Search
CPC ..... A61B 5/681; A61B 5/0015; A61B 5/0017; A61B 5/0022; A61B 5/6898; G16H 20/30;
(Continued)

(56) References Cited

U.S. PATENT DOCUMENTS 7,167,417 B2   1/2007 Akahane et al.
8,761,448 B1 *  6/2014 Burr ..................... G06F 3/0304
                                                382/103
(Continued)

FOREIGN PATENT DOCUMENTS

EP    1 553 469 A1    7/2005
EP    2 458 458 A1    11/2010
(Continued)

OTHER PUBLICATIONS

Non-English Language International Search Report and Wratten Opinion for PCT/IB2017/054084 dated Oct. 16, 2017, 6 pages.

*Primary Examiner* — Qun Shen
(74) *Attorney, Agent, or Firm* — Blank Rome LLP

(57) ABSTRACT

The invention relates to a method for measuring and displaying data linked to a person's physical activity, comprising: measuring data linked to the person's physical activity using a mechanical sensor in a wrist watch worn by the person; displaying the measured data on the watch face; taking an image of the watch face using a camera in an electronic device; analysing the image in order to determine the data; processing the data so as to process the analysed data; and displaying the processed data on a screen of the electronic device.

13 Claims, 1 Drawing Sheet

(51) Int. Cl.
  *G01C 22/00* (2006.01)
  *G04B 47/06* (2006.01)
  *G16H 40/63* (2018.01)
  *G16H 30/40* (2018.01)
  *G16H 40/67* (2018.01)

(52) U.S. Cl.
  CPC .......... *A61B 5/0022* (2013.01); *A61B 5/6898* (2013.01); *G01C 22/006* (2013.01); *G04B 47/063* (2013.01); *G16H 20/30* (2018.01); *G16H 30/40* (2018.01); *G16H 40/63* (2018.01); *G16H 40/67* (2018.01); *A61B 2562/0219* (2013.01)

(58) Field of Classification Search
  CPC ........ G16H 40/67; G16H 30/40; G16H 40/63; G01C 22/006
  See application file for complete search history.

(56) References Cited

U.S. PATENT DOCUMENTS

| | | | |
|---|---|---|---|
| 9,383,725 B2 | 7/2016 | Willemin et al. | |
| 2005/0105401 A1* | 5/2005 | Akahane | G04R 60/14 368/187 |
| 2013/0234850 A1* | 9/2013 | Lee | A61B 5/681 340/539.12 |
| 2013/0329040 A1* | 12/2013 | Willemin | G04D 7/12 348/135 |
| 2016/0070236 A1 | 3/2016 | Willemin et al. | |
| 2016/0259299 A1* | 9/2016 | Kahn | G04B 47/063 |
| 2017/0102672 A1* | 4/2017 | Martin | G04G 21/04 |
| 2017/0118639 A1* | 4/2017 | Beale | H04W 12/06 |

FOREIGN PATENT DOCUMENTS

| | | |
|---|---|---|
| JP | 2008197732 A | 8/2008 |
| JP | 2014503801 A | 2/2014 |
| JP | 2015082219 A | 4/2015 |
| WO | WO 2005/003867 A1 | 1/2005 |
| WO | WO 2012/069444 A1 | 5/2012 |
| WO | WO 2013/134713 A1 | 9/2013 |

* cited by examiner

METHOD AND SYSTEM FOR MEASURING AND DISPLAYING DATA LINKED TO A PERSON'S PHYSICAL ACTIVITY

RELATED APPLICATIONS

This application is a national phase of PCT/IB2017/054084 filed on Jul. 6, 2017, which claims the benefit of Swiss Application No. 00872/16, filed on Jul. 7, 2016 and Swiss Application No. 00216/17, filed on Feb. 24, 2017, The entire contents of these applications are hereby incorporated by reference.

TECHNICAL FIELD

The present invention relates to measuring the physical activity of people using wristwatches.

STATE OF THE ART

Wristwatches and other devices worn on the wrist are known in the state of the art for determining the physical activity of the wearer. Some electronic watches are for example provided with a step counter that determines the number of steps performed by the wearer. Other sport watches can display the distance traveled during a race, the altitude difference, or other parameters related to physical activity.

These parameters can be displayed on the screen of the watch or of the bracelet. Connected watches ("smartwatches") also make it possible to transmit them, for example via a wired or wireless interface, to a computer or smartphone so that they can be displayed and manipulated more comfortably. Connected watches are known that communicate via a Bluetooth interface with a nearby smartphone. This smartphone allows the results to be displayed and memorized.

W013134713 advocates that communication between an electronic watch provided with biometric sensors and a smartphone is performed through an optical communication protocol. The image sensor of the smartphone captures an image of the watch face presenting a tag, for example in the form of a QR code, and extracts data from it.

These solutions are, however, reserved for electronic watch devices and that have a battery to power the communication interface. They are therefore not applicable to mechanical watch devices comprising only analog indicators, for example hands or rotating discs.

Many consumers, however, appreciate the elegance of mechanical watches and the fact that they must not be recharged or even rewound in the case of automatic watches. Mechanical watches don't only display the current time; they often have other complications to measure and display parameters not related to the current time. At present, these additional parameters are only displayed and processed in the watch, without the comfort and power of electronic processing provided in a computer or smartphone.

BRIEF SUMMARY OF THE INVENTION

An object of the present invention is therefore to propose a method for displaying on an electronic equipment non-time-related data measured with a mechanical watch.

In particular, an object of the present invention is therefore to provide a method for displaying on an electronic equipment data related to physical activity and measured with a mechanical watch.

According to one aspect, this goal is achieved through a method of measuring and displaying data representative of a person's physical activity, comprising:

measuring data representative of the physical activity of the person by means of a mechanical sensor in a wristwatch worn by the person;

displaying these measured data on the dial of the wristwatch by means of an analog indicator;

capturing the image of said dial by means of a camera in a portable electronic equipment;

analyzing said image to determine the position of said analog indicator, with said position constituting one or more analyzed data;

processing, in the portable electronic equipment, said analyzed data, so as to determine data representative of the physical activity processed;

displaying the processed representative physical activity data on a screen of the electronic equipment.

The analog indicator may comprise for example a hand or a rotating disc.

The method therefore implements a camera and an electronic equipment to capture an image of the mechanical watch and to determine the position of the analog indicator, and thus the measured data, by means of image analysis.

The portable electronic equipment can be for example a smartphone, a tablet, an electronic smart watch (smartwatch), connected eyeglasses, or other personal equipment intended to be carried by a user during his daily activities, for example by wearing it on the body or in a pocket.

This solution has notably the advantage over the prior art of avoiding the need for electronic components, a connector or antenna, and a battery in the mechanical watch.

For this purpose, the data representative of the physical activity can for example be determined by an integration of the oscillations undergone by an oscillating mass since a time of zeroing, or per unit of time.

The data displayed on the dial of the watch are therefore determined purely mechanically. Due to mechanical limitations, the accuracy of these data is limited, and the nature of the data is restricted.

The limitation of accuracy comes, for example, from variability due to the manufacturing process, environmental factors (temperature, gravity, shocks), etc.

The restrictions related to the nature of the data come simultaneously from the difficulty of performing complex calculations with mechanical means. The mechanical display in the watch is nevertheless very useful as a first indication, always available even in the absence of any power source or when the portable electronic equipment is not available.

Data processing by portable electronics can be used to improve their accuracy, for example to compensate for or correct predictable errors, such as bias.

The data processing by the portable electronics can be used to display data representative of the different physical activity, which are not the data displayed on the watch, but which are deduced from the data displayed by the watch.

As an example of application, a runner may use the mechanical watch to obtain, during the race, an indication of the number of steps performed, obtained by mechanical means. After his race, he can read the data displayed on the dial of his watch with his smartphone, and obtain on the one hand a more precise evaluation of the number of steps (for example by correcting known bias or bias specific to the watch), and, on the other hand, additional processed data, for example a distance traveled, a number of calories expended, etc.

The position of the indicator may be represented for example by one or more digits, for example a numerical value pointed by a hand, an angle relative to a reference position, the angle of two hands, etc. We are thus talking about data.

An image analysis has already been implemented to check the position of the hands of a watch and that it is running well. By way of example, WO012069444A1 relates to a method for determining the running deviation of a mechanical watch with an image analyzer. Similarly, WO05003867 relates to a time correction system for a watch with hands by means of a camera that captures images of the dial, and a system that analyzes these images to determine the time displayed by the watch. These solutions only make it possible to check whether the time indicated by a mechanical watch is accurate; they are of no use in transmitting other data.

The need to analyze the position of the analog indicators of a watch has therefore only been felt for the purposes of corrections or for checking the running of a watch; in this case, the point is to compare the measurement of the time performed by the watch with a supposedly more accurate measurement performed by a complex electronic system. However, these documents do not describe how it might be useful to transmit, to electronic equipment external to the watch, physical activity data that does not require or that cannot be verified.

In any case, this prior art does not suggest a wristwatch having a mechanical sensor of physical activity. The usual physical activity counters, notably step counters, conventionally employ an electronic accelerometer, for example based on a MEMS circuit.

Data representative of physical activity is meant, in the present application, to be understood as data whose primary function is to inform the wearer of the watch about the efforts made during a physical activity. Data are said to be representative of the physical activity of a person when they are intended to determine the level of physical activity of the person and to indicate whether this activity is sufficient, for example as part of a training or fitness program, or if it needs to be increased. The physical data may comprise, for example, an estimate of the number of steps taken, a distance traveled, an energy expended since the beginning of the measurement, or an energy per unit of time.

Mechanical sensor is meant to be understood, in the present invention, as a sensor whose operation is exclusively mechanical and therefore does not require electrical or electronic component.

The method advantageously comprises the following steps:
storing person-specific parameters in a memory space;
with said data processing using said person-specific parameters for determining said representative physical activity data processed in a personalized manner for the person.

The memory space may be a memory space of the portable electronic equipment, or a memory space accessible by the data processing equipment or module.

This method thus makes it possible to measure physical parameters in a fully mechanical manner, by means of a mechanical sensor in a mechanical wristwatch, and then to determine the displayed data customized according to the user thanks to the processing flexibility of the portable electronic equipment.

In one embodiment, the data measured in the mechanical wristwatch correspond to oscillations or alternations of an oscillating weight. The wristwatch displays a value which depends on this number of oscillations or alternations, and which may for example correspond to a number of steps. The portable electronic device determines the value indicated by image analysis, then processes it according to personalized parameters such as for example the size of the user, the average length of his strides, his weight, etc., in order to determine and display other processed data, such as for example the distance traveled, the number of calories burned, the number of floors climbed, etc.

The method advantageously comprises the following steps:
storing calibration parameters specific to the wristwatch in a memory space;
with said data processing using said calibration parameters specific to the wristwatch to determine said representative physical activity data calibrated for the wristwatch.

The portable electronic equipment can thus correct any measurement errors specific to the wristwatch.

The calibration parameters can for example be determined by comparing a series of measurements made with the wristwatch and comparable measurements made with the portable electronic device.

The mechanical sensor may be a mechanical motion sensor integrated in the wristwatch.

The mechanical sensor can be a sensor that counts the number of oscillations.

The mechanical sensor can be a sensor that takes into account the number and amplitude of the oscillations.

The mechanical sensor can be an oscillation sensor when walking.

The motion sensor can be a pedometer. The data then depend on the number of steps taken by the person.

The method may include a step of automatically and periodically zeroing the data displayed on the dial.

The method may include a step of manually zeroing the data displayed on the dial.

In one embodiment, the displayed data are incremented with each movement of the wearer or with each movement of the wearer in a given direction or orientation, and only decremented by voluntary action of the user or automatically at periodic intervals.

The invention also relates to a system for measuring and displaying data representative of a person's physical activity, comprising:
a wristwatch equipped with a mechanical sensor for capturing data related to the physical activity of the person when wearing the wristwatch, and an analog indicator for displaying these data on a dial of the wristwatch;
portable electronic equipment with a camera;
a module for analysing the images captured by said camera, for determining the data displayed on the dial when the image includes a picture of the dial;
a processing module for processing said data determined by the image analysis module;
a module for displaying the processed data on a screen.

According to one aspect, the invention also relates to a computer data medium comprising a program executable by an electronic equipment so that said equipment processes and displays data related to the physical activity of a person, said program comprising:
a module for image capture;
a module for analysing the captured images, for determining the data displayed on the dial when the image includes a picture of the dial;
a processing module for processing said data determined by the image analysis module;

a module for displaying the processed data on a screen.

The electronic equipment can be a smartphone, a tablet, a computer, etc.

The embodiments described for the method according to the invention apply to the system and to the data carrier according to the invention and vice versa, mutatis mutandis.

BRIEF DESCRIPTION OF THE FIGURES

Examples of implementation of the invention are indicated in the description illustrated by the appended figures in which.

EXAMPLE(S) OF EMBODIMENT OF THE INVENTION

Figure 1:
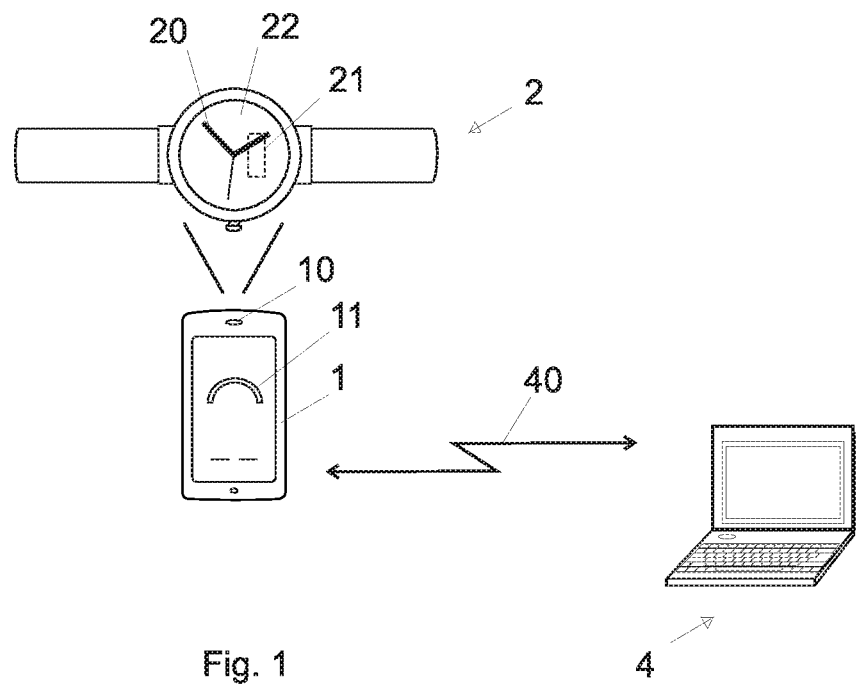
FIG. 1 illustrates an exemplary system according to the invention.

An exemplary system according to the present invention is illustrated in FIG. 1. The system comprises an electronic equipment 1 and a mechanical wristwatch 2.

The electronic equipment 1 can be for example a smartphone, a tablet, etc., with a screen 11 and a camera 10 to capture still images or animated images (videos). An optional wired or wireless interface, for example a wifi or Bluetooth interface, makes it possible to connect it to external equipment, for example a computer, and/or to the Internet.

The wristwatch 2 is provided with an analog indicator 20, for example an indicator with hands, with discs, with rollers, with retractable beacons, or with another part of the movement, to display the current time as well as non-time related data, such as data related to the physical activity of the person wearing the watch.

These data are obtained by means of a mechanical sensor 21 integrated in the wristwatch. The sensor may be part of the movement of the watch, or an auxiliary module superimposed on the main movement.

In one embodiment, these data depend on accelerations of the watch when the wearer of the watch moves his wrist. It is possible to measure for example the maximum acceleration since a reset-to-zero time, which gives an indication of force, or the accumulated acceleration which gives an indication of the work done.

These accelerations can be measured with a test mass in the mechanical sensor, i.e. a mass made to rotate, in oscillation or in translation, by the movements of the person. This mass can be a mass different from the oscillating weight whose function is the automatic rewinding of the watch. In one embodiment, this mass is the oscillating mass of the movement, whose oscillations are counted mechanically in order to derive information other than the power reserve and relating to the physical activity of the wearer.

An unrepresented integrator adds the oscillations or alternations undergone by the test mass to deduce data representative of the activity of the person. In one embodiment, this integrator comprises a spring, for example a spiral spring, or another deformable element, which is tensioned at each oscillation of the test mass, or at each oscillation whose amplitude exceeds a threshold, or at each oscillation in a given direction. The deformable element relaxes automatically, for example every day at midnight, or manually under the action of a push-button, or continuously. The spring tension then depends on the number of oscillations since the manual or automatic zeroing, and possibly on the amplitude of these oscillations; it can be displayed to indicate a measure of the energy expended by the user since the reset.

It is also possible to use a counter as an integrator, for example a digital counter, the value of which is incremented at each oscillation.

In these embodiments, the data therefore represent an integration of the accelerations experienced by the wristwatch 2 during a given period. This data may for example depend on the number of steps taken by the person.

A reset-to-zero module, not represented, makes it possible to reset the counter periodically, for example whenever the time indicated by the movement of the watch corresponds to midnight, or each time the movement moves from a phase of intense activity at a less intense activity phase, or vice versa. A manual reset module, for example using a push button or a position of the crown, can also be used. It is also possible to reset a counter when the user removes his watch, for example to sleep, and no movement is detected for a specified period.

The measured data displayed are displayed on the dial 22, for example by means of a hand assigned to this display, or another appropriate analog indicator. It is also possible to display a value by means of several hands.

Figure 2:
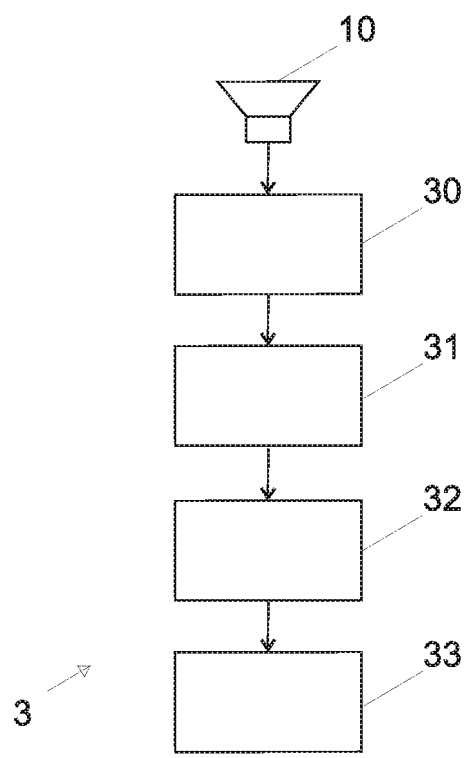
FIG. 2 is a block diagram of the main modules of an apparatus according to the invention.

The portable electronic equipment comprises an electronic program, for example an app or another executable, described in connection with FIG. 2. The element 10 corresponds to the camera already described. An image capture module 30, which may be distinct from the program, makes it possible to capture images of the dial 22, or other images.

An image analysis module 31 receives the images captured with the camera 10 and analyzes them by means of an algorithm of image recognition, in order to determine the data related to the activity of the person displayed in an analog manner on the dial when the analyzed image includes a picture of this dial.

For this purpose, the module 31 may include a preprocessing module for adjusting the contrast, the brightness, and/or the white balance of the image. Preprocessing may also include perspective correction in case the image is taken from a direction non-perpendicular to the dial, which makes it possible to correct parallax errors; to this effect, it may be advantageous to provide a reference shape on the dial 22, for example a rectangular shape or the like, known by the pretreatment module which can correct the trapezoidal deformations in order to correct the errors of perspective.

A reframing module isolates and orients the rectified image portion comprising the dial 22, or in any case the indicator (for example the hand and the associated indexes) which displays the relevant data on this dial.

The analysis module 31 also includes a module for extracting elements ("feature extraction") in order to extract the desired elements of the image, in particular the indicators, for example the hands or the end of those. A module for determining the position of these features then makes it possible to determine the angle of the identified hand, or the angular or longitudinal position of another indicator, to directly deduce the displayed physical activity data.

The data thus determined are transmitted to a processing module 32 which processes them in order to determine processed data and then to display them.

The processing may for example include a correction of the data displayed on the wristwatch. The correction may take into account, for example, calibration data previously determined and specific to the wristwatch and/or to the person. In one embodiment, the method comprises a prior step of comparing the physical parameters measured by the wristwatch and by the portable electronic equipment during the same physical effort, then of determining a table or a correction function according to the results of this comparison. It is thus possible to correct a systematic bias in the measurement of the portable electronic equipment.

The treatment may include the determination of values personalized according to the person, using personalized parameters stored in a memory space of the wristwatch. In one embodiment, the processing module uses for this purpose data previously introduced by the wearer of the watch, for example his weight, his height, the length of his strides, his age, his type, his objectives, the type of physical activity, etc. From a number of steps displayed on the wristwatch and these personalized parameters, it is thus possible to determine for example a distance traveled or a number of calories consumed, according to a calculation customized for the person.

The processing may also include, for example, the storage, the comparison with previous data or with reference data, and/or the calculation of other data from the raw data thus determined.

Other data used by the module 32, such as meteorological data, comparisons with other users, etc., can be drawn from a communication network, for example the Internet.

A display module 33 then makes it possible to display the data thus processed on a screen 11 of the electronic equipment 1, or on another screen. The data can also be rendered in a sound form.

The measured and displayed data may for example comprise a number of steps, an index of activity (or inactivity) or a number of calories achieved respectively spent since the last reset of the counter of the watch. In on variant, it is possible to display a percentage of activity with respect to a goal defined by the user or proposed by the program.

Several displays can be provided. For example, a first display may indicate a datum representative of the number and the amplitude of the oscillations since a time of zeroing; the value therefore depends on the physical energy expended, or the number of steps taken, since this reset, for example since midnight. A second display may for example be incremented at each displacement, and decremented regularly with the flow of time measured by the movement of the watch; the displayed value therefore corresponds to a power expended.

It is also possible to calculate and display a number of hours of sleep, of light physical activity, or of intense physical activity. A sleep phase can be detected by the mechanical sensor and/or by the treatment module when the motion sensor detects low physical activity for a prolonged period; the probability of sleep is even greater if this low activity occurs at night. For this purpose, the mechanical sensor can be designed to detect the passages between phases of sleep, light activity and intense activity; the times of passage, or the durations, can be displayed on the dial of the watch.

These data can be displayed as text, numbers and/or diagrams. They can also be saved or transmitted to other devices remotely.

The invention claimed is:

1. Method for measuring and displaying data related to a physical activity of a person, comprising:
  measuring data representative of the physical activity of the person by means of a mechanical sensor in a mechanical wristwatch worn by the person, wherein the working of the mechanical sensor is exclusively mechanical;
  displaying these measured data on a dial of the mechanical wristwatch by means of an analog indicator, said analog indicator being a hand or rotating disc;
  capturing the image of said dial by means of a camera in a portable electronic equipment;
  analyzing said image to determine the position of said analog indicator, with said position constituting one or more analyzed data;
  processing, in the portable electronic equipment, said analyzed data, so as to determine data representative of the physical activity processed;
  displaying the processed representative physical activity data on a screen of the electronic equipment
  the method further comprising
  storing calibration parameters specific to the mechanical wristwatch in a memory space of the portable electronic equipment;
  with said data processing using said calibration parameters specific to the mechanical wristwatch to determine said representative physical activity data calibrated for the mechanical wristwatch
wherein the mechanical sensor comprises a test mass and an integrator
wherein the integrator is configured to add the oscillations or alternations undergone by the test mass to deduce data representative of the activity of the person.

2. Method according to claim 1, further comprising:
  a step of storing person-specific parameters in a metnory space;
  with said data processing using said person-specific parameters for determining said representative physical activity data processed in a personalized manner for the person.

3. Method according to claim 1, said mechanical sensor being a motion sensor, such as a pedometer or an accelerometer, wherein the working of the mechanical sensor is exclusively mechanical.

4. Method according to claim 3, comprising a step of integrating the movements undergone by the motion sensor since a time of reset, and displaying by means of said analog indicator a value corresponding to this integration.

5. Method according to claim 2, said processed data using the parameters specific to the person indicating a distance traveled and/or a number of calories spent.

6. Method according to claim 1, comprising a step of automatically and periodically zeroing the data displayed on the dial, or a step of manually zeroing the data displayed on the dial.

7. Method according to claim 1, wherein the displayed data are incremented with each movement of the wearer or with each movement of the wearer in a given direction or orientation, and only decremented by a voluntary action of the user or automatically at periodic intervals.

8. System for measuring and displaying data related to a physical activity of a person, comprising:
  a mechanical wristwatch, said mechanical wristwatch comprising a. mechanical sensor for capturing data related to the physical activity of the person when wearing the mechanical wristwatch, wherein the working of the mechanical sensor is exclusively mechanical, a dial, and an analog indicator for displaying these data on said dial, said analog indicator being a hand or a rotating disc;
  portable electronic equipment, said portable equipment comprising;
  a camera
  a screen;

a module for analysing the images captured by said camera for determining one or more analyzed data corresponding to the data displayed on the dial when the image includes a picture of the dial;

a processing module for processing said data determined by the image analysis module and for generating the processed data;

a module for displaying the processed data on said screen said portable electronic equipment comprising a memory space of the portable electronic equipment, for storing calibration parameters specific to the mechanical wristwatch;

said data processing module using said calibration parameters specific to the mechanical wristwatch to determine said representative physical activity data calibrated for the mechanical wristwatch wherein the mechanical sensor comprises a test mass and an integrator wherein the integrator is configured to add the oscillations or alternations undergone by the test mass to deduce data representative of the activity of the person.

9. System according to claim 8, said mechanical sensor being a motion sensor, such as a pedometer or an accelerometer.

10. System according to claim 8, said mechanical wristwatch comprising a member for automatically and periodically zeroing the data displayed on the dial or a member for manually zeroing the data displayed on the dial.

11. System according to claim 8,:

said portable electronic equipment comprising a memory space for storing person-specific parameters;

said data processing module being designed for using said person-specific parameters for determining said representative physical activity data processed in a personalized manner for the person.

12. Method according to claim 1, wherein the integrator comprises a spring or another deformable element, which is tensioned at each oscillation of the test mass, or at each oscillation whose amplitude exceeds a threshold, or at each oscillation in a given direction.

13. System according to claim 8, wherein the integrator comprises a spring or another deformable element, which is tensioned at each oscillation of the test mass, or at each oscillation whose amplitude exceeds a threshold, or at each oscillation in a given direction.

* * * * *